United States Patent

Wang

[11] Patent Number: 5,533,985
[45] Date of Patent: Jul. 9, 1996

[54] TUBING

[76] Inventor: James C. Wang, 15 Massasoit Ave., Norton, Mass. 02766

[21] Appl. No.: 230,333

[22] Filed: Apr. 20, 1994

[51] Int. Cl.$^6$ .................................................. A61M 25/00
[52] U.S. Cl. ........................... 604/264; 604/282; 128/656
[58] Field of Search ..................................... 604/282, 280, 604/281, 96, 264; 128/656–658, 786

[56] References Cited

U.S. PATENT DOCUMENTS

| | | |
|---|---|---|
| 4,250,072 | 2/1981 | Flynn . |
| 4,283,447 | 8/1981 | Flynn . |
| 4,739,768 | 4/1988 | Engelson . |
| 4,863,442 | 9/1989 | DeMello et al. ......................... 604/282 |
| 5,005,587 | 4/1991 | Scott ....................................... 128/786 |
| 5,125,913 | 6/1992 | Quackenbush . |
| 5,156,857 | 10/1992 | Wang et al. . |
| 5,167,647 | 12/1992 | Wijkamp . |
| 5,221,270 | 6/1993 | Parker ..................................... 604/282 |
| 5,279,596 | 1/1994 | Castaneda et al. ..................... 604/282 |
| 5,308,342 | 5/1994 | Sepetka et al. ......................... 604/282 |

OTHER PUBLICATIONS

Paper published by J. G. Schwaegerle and W. R. Deaton at the 1993 SPE (Society of Plastics Engineers), Antec Meeting (May 1993).
Putnam Plastics Corporation's advertisement.

*Primary Examiner*—John D. Yasko
*Attorney, Agent, or Firm*—James C. Nemmers

[57] ABSTRACT

Differential stiffness tubing for medical products, such as catheters, and a method and apparatus for making the tubing. The tubing has a stiff section and a flexible section joined by a relatively short transition section in which the materials of the stiff and flexible sections are wedged into each other in a smooth gradual manner to produce an inseparable bond between the materials without abrupt joints. The tubing is made using a resin modulating system and a unique co-extrusion head that minimize the length of the transition section by minimizing the volumes in all flow channels of the head.

26 Claims, 13 Drawing Sheets

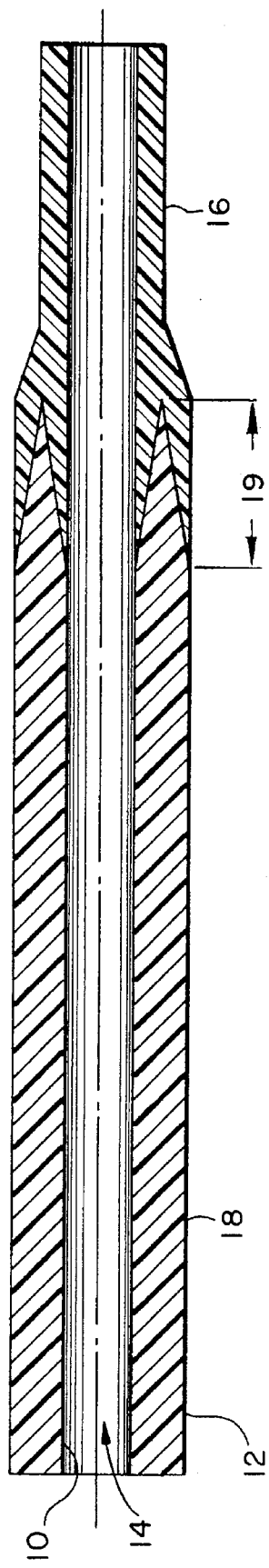
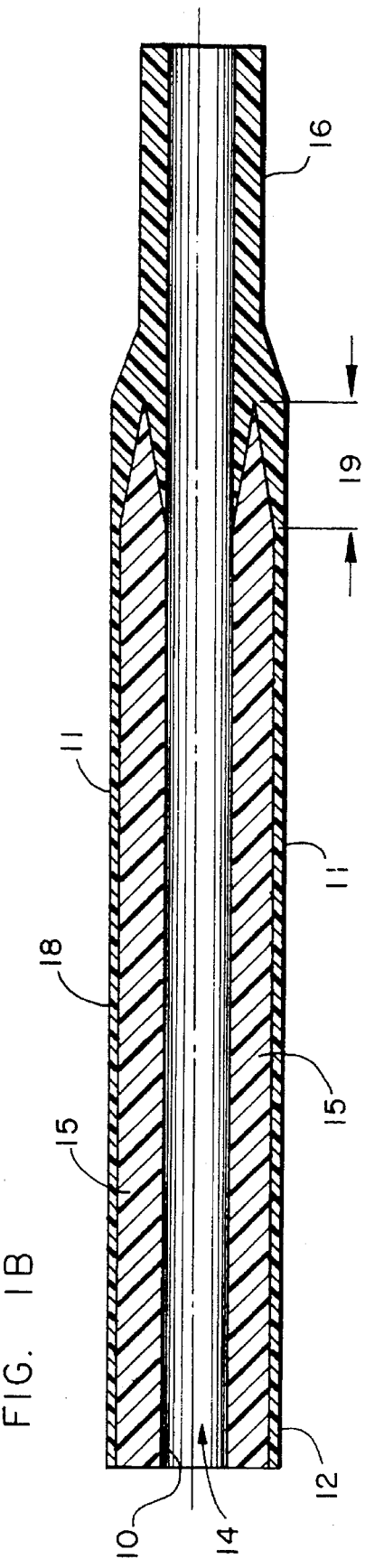
FIG. 1A
FIG. 1B

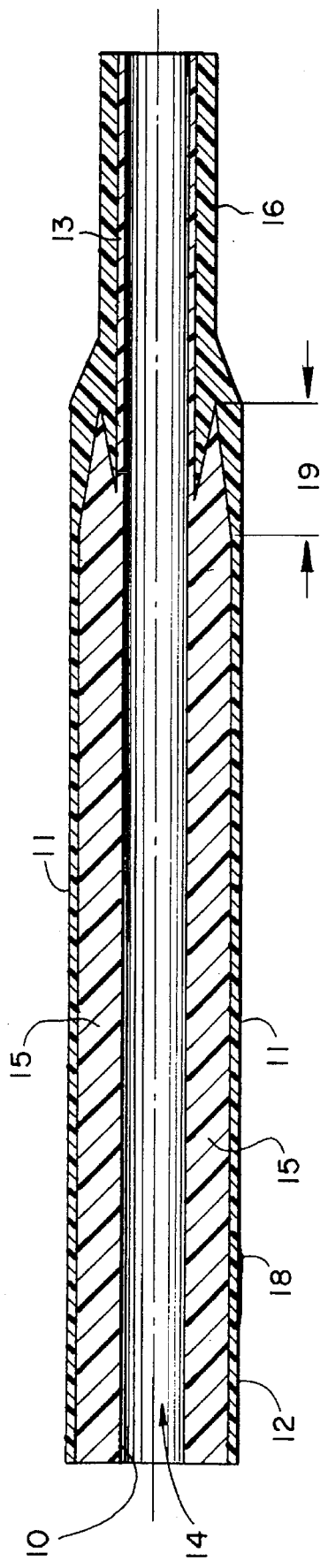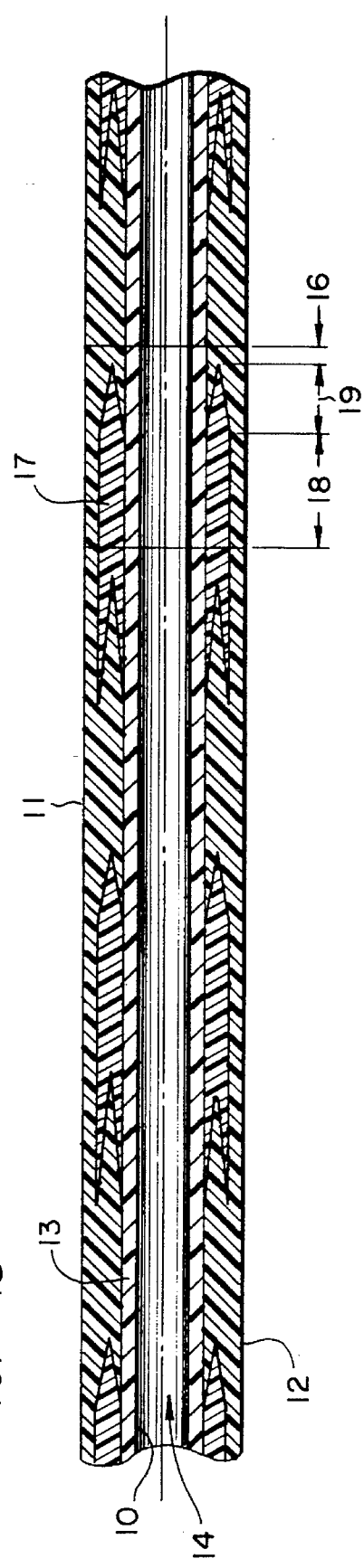

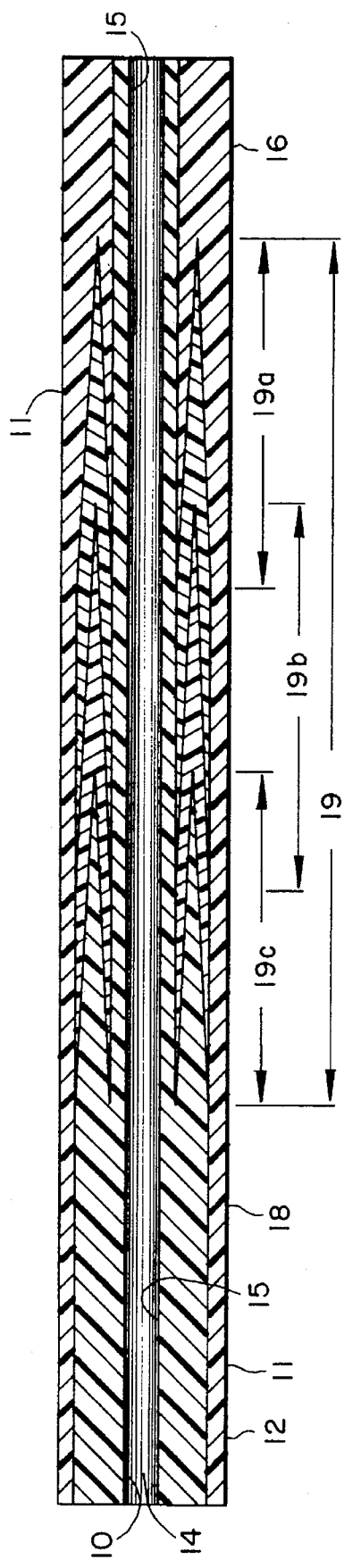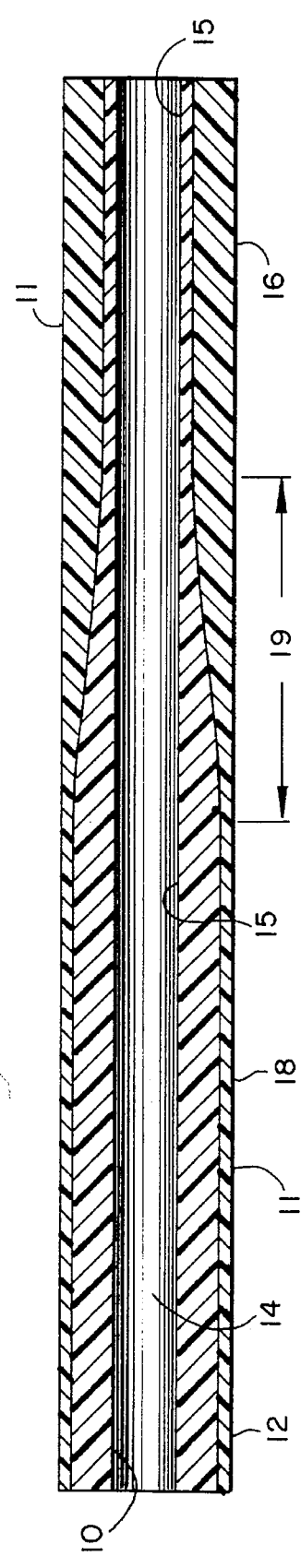

TUBING

BACKGROUND OF THE INVENTION

Catheters are used in the field of medicine in a variety of medical and surgical procedures. For example, catheters are used extensively for delivering diagnostic or therapeutic agents to a selected site within the body. Microcatheters are used in neurointerventional and similar procedures. These catheters are commonly threaded through a vessel or artery and frequently follow a tortuous path in order to reach the site where the agent is to be applied. A balloon catheter for treating, for example, arterial stenosis has an inflatable balloon at its distal end. This catheter also follows a tortuous path to reach the site of the arterial restriction. The balloon is then inflated via a lumen through the shaft of the catheter, applying pressure to expand the stenosis against the artery wall.

Because these catheters often must be threaded through a tortuous path, the catheters must be rigid enough to allow the distal end of the catheter to be manipulated by the physician or surgeon. On the other hand, the catheter must be quite flexible to permit it to follow the tortuous path to the desired site of application. In order to satisfactorily meet the requirements of flexibility and also stiffness for manipulation, various designs of catheters are known and used. One such catheter utilizes a flexible catheter with an inflatable balloon at its distal end which, when partially inflated, will be carried by the blood flow to the desired location. Such catheters, however, cannot be used if the site where the agent is to be applied can be accessed only through a vessel that has a low blood flow rate.

More commonly, guide wires are used which can be advanced to the site, and with the guide wire in place, the catheter can then be telescoped over the wire and advanced to the application site. Catheters that use the guide wire technique, however, still must be sufficiently flexible to track the wire and sufficiently rigid so that the catheter can be advanced without buckling at the proximal end.

In order to overcome these limitations and difficulties, differential stiffness catheters have been developed which have different degrees of flexibility throughout their length. These catheters have a long and stiff proximal section coupled to a short and soft or flexible distal section that will track the guidewire. With these differential stiffness catheters, the physician or surgeon can push and maneuver the stiff proximal end to effectively advance the soft distal end. For example, Engelson U.S. Pat. No. 4,739,768 discloses a catheter which has a relatively stiff proximal segment and a relatively flexible distal segment, the segments being formed by forming the proximal segment of inner and outer coaxial tubes, one of which is relatively stiff, and the other of which is relatively flexible. The distal segment is then merely an extension of the relatively flexible tube.

Because this type of differential stiffness catheter is usually made by hand by joining two or more pieces of tubing together, they are labor intensive and therefore expensive to manufacture. Moreover, these catheters tend to buckle and to kink at the joints where there occurs an abrupt change in stiffness. Buckling and kinking are very undesirable characteristics for catheters. Also, there is a tendency for the joints to separate leaving the tip of the catheter inside the body and requiring surgery to retrieve it. Attempts have been made to reduce the buckling and kinking problems and prevent joint separation by making the catheter with a relatively soft layer throughout the entire length of the catheter, but this construction results in reduced stiffness at the proximal end.

Prior art patents such as Quackenbush U.S. Pat. No. 5,125,913 and Flynn U.S. Pat. Nos. 4,250,072 and 4,283,447 recognized some of the potential benefits of using a process technology called co-extrusion to make variable stiffness catheters. However, disappointing results have been obtained in following their teachings. Co-extruded catheters produced by periodic interruption using prior art teachings result in undesirably long transition sections, which are the sections of the catheter where the tubing changes from a stiff tube to a soft tube. Some of the catheters produced by these prior art processes have transition sections that extend the entire length of the catheter. These undesirably long transition sections have been the major problem in attempts to make catheters and other medical tubing with interrupted layers or interrupted elements. Also, the interrupted layers co-extrusion process results in only a moderate difference in stiffness between the proximal and distal sections—less than is considered desirable for catheters. Moreover, since very long cycle times are required for known interrupted layer processes, these co-extrusion processes are not as economically feasible as first thought. Further study has shown that these deficiencies cannot be corrected by simple means, such as process variable changes, but rather require fundamental changes in the process itself.

Furthermore, the prior art does not recognize the possibility of forming a very secure joint between soft and stiff resins by using co-extrusion and sequential extrusion processes to produce a "wedged-in" transition section in which one resin is securely locked or wedged into another resin.

In addition to the foregoing, medical catheters must have the proximal end attached to a variety of different connectors which facilitate attachment of one or more medical device or devices necessary to carry out the particular medical procedure using the catheter. At the point of attachment of the catheter tube to the connector, kinking can easily occur and restrict the flow of the fluid being introduced into the catheter tube. To minimize the probability of kinking, prior art catheters commonly use a short length of a flexible rubber tube that extends from the connector and into which the proximal end of the catheter is inserted and affixed. Although use of this rubber tube reduces kinking of the catheter tube, there is still considerable strain applied to the catheter tube at the point where it exits the rubber tube connector. This kinking problem also exists in tubing used in nonmedical applications.

It is therefore an object of the invention to develop a co-extrusion method of forming tubing such as catheters in which the transition section can be shortened and controlled to the point where a variety of suitable medical catheters with interrupted layers and elements can be properly produced at a reasonable cost.

It is another object of the invention to develop a method of forming the "wedged-in" construction in the transition section of the tubing to produce an extremely secure joint between different resins.

It is yet another object of the invention to use the methods of the invention to provide an improved strain relief section where the tubing is joined to a connector or other device thereby eliminating kinking at this joint.

It is a further object of the invention to develop a suitable co-extrusion head and system to carry out the methods of the invention.

SUMMARY OF THE INVENTION

The invention relates to the manufacture of a tubing having different properties, for example differential stiffness, in different sections along its length. Such tubing is useful in many medical applications, such as catheters. A catheter made utilizing the principles of the invention has a stiff proximal section for "pushability", a flexible, soft distal section for tracking the guidewire and a unique transition section of controlled length, e.g., significantly shorter than is possible with prior art extrusion fabrication methods, in which the stiff material of the proximal section and the flexible material that forms the distal section are sequentially co-extruded, e.g., "wedged into" one another to produce an extremely secure, practically non-breakable joint between the two materials. The merging of the two materials is very smooth and gradual to eliminate the buckling and kinking that usually occurs at abrupt joints between two materials of different stiffness. The gradual transition also facilitates tracking of the guidewire and is short enough to be useful in catheter applications, including so-called microcatheters. Typically, the average length of the transition section in such medical catheter tubing is about 0.25–20 inches, preferably about 0.5–10 inches.

Tubing produced according to the invention for medical applications is extremely small in diameter and wall thickness and cannot be produced practically by hand. Therefore, in another aspect of the invention, a low cost automatic co-extrusion process and co-extrusion head are provided. The co-extrusion head is designed to minimize volumes for all the flow channels, within limits discussed further below, and has no moving parts which is essential to precisely control the diameter of the tubing and to assure consistently high quality of the final product. The design of the co-extrusion head also provides for virtually mutual exclusivity of resins, i.e., it is possible to produce a tubing that has virtually 100% of the stiff resin in the proximal section and virtually 100% of the soft resin in the distal section. Moreover, the method and system of the invention provide for the production of tubing using several thermoplastic resins of varied stiffness which can be automatically fed into the co-extrusion head in a precisely synchronized fashion to produce a tubing having different resins or resin combinations in different sections of the tubing, always with gradual transitions from one to the other in short transition sections.

All of the foregoing, as well as other features of the invention, will become more readily apparent from the detailed description of the preferred embodiments of the invention as illustrated in conjunction with the accompanying drawings.

BRIEF DESCRIPTION OF THE DRAWINGS

FIGS. 1A, 1B, 1C, 1D, 1E and 1F are longitudinal cross-sectional views of a portion of differential stiffness catheters of the type to which the invention relates;

DETAILED DESCRIPTION OF THE PREFERRED EMBODIMENTS OF THE INVENTION

In order to fully and completely understand the co-extrusion and sequential extrusion of differential stiffness tubing, certain terms and phrases that are used herein must be clearly understood. The terminology used herein is that commonly used and understood by those ordinarily skilled in the art unless otherwise indicated or as modified by the specific definitions set forth in this specification. When the terms "outside layers" or "inside layers" are used herein, these refer to the inside layer and outside layer of the tube, and sometimes these are referred to simply as the "side layers". The "interior layers" are all the layers that form a tube other than the side layers.

Figure 9A:
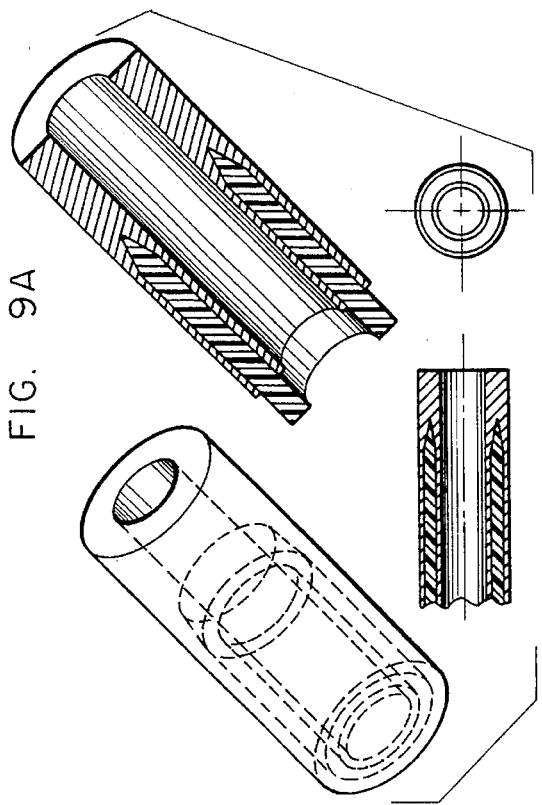
FIGS. 9A and 9B each contain various views of a catheter end to illustrate the differences between a layer construction and an elements construction.
Figure 9B:
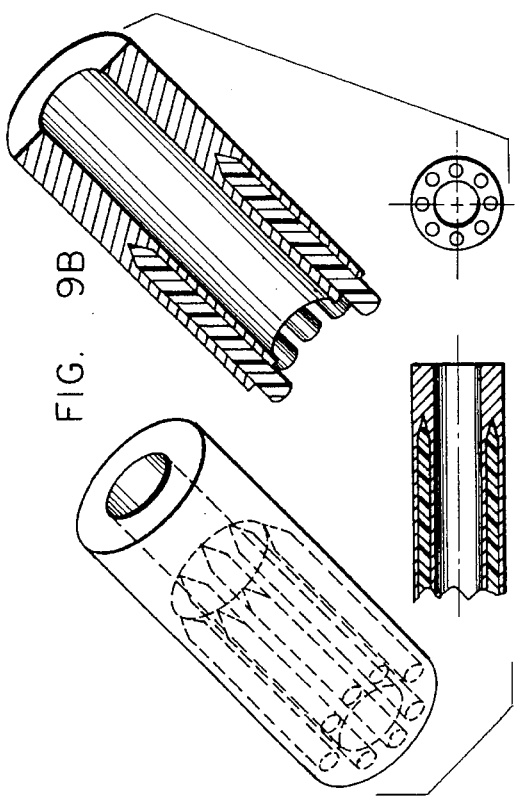

Also, as used herein, the word "elements" means any shape that is not continuous in the cross-sectional direction of a tube, such as the construction illustrated in FIG. 9B. The cross-sectional shape of the elements can be round as shown, or they can be rectangular or any other shape.

In FIGS. 1A, 1B, 1C, 1D, 1E and 1F, there are illustrated differential stiffness catheters of the type to which the invention relates. Such catheter tubing is typically of an outside diameter of about 0.25–0.02 inch. The tubing and process described herein are most valuable for catheters no larger than 0.08 inch outside diameter. In each of these drawing figures, the diameter has been greatly enlarged and the length compressed so as to clearly show the different layers between the catheter walls. The catheters shown in FIGS. 1A, 1B, 1C, 1D, and 1F each have an inner wall 10 and outer wall 12 that define an annular tube with a longitudinally or axially extending passageway 14 through which a guidewire (not shown) can be passed and through which fluid flows. As is well known to those skilled in the art, the catheter has a distal section 16 which is commonly the soft or flexible portion of the tube and a proximal section 18 which is the stiff portion of the tube. As shown in FIGS. 1A–1F, the "transition section" 19 is the length of the catheter in which the tube changes from a stiff tube to a soft tube. The term "transition section is defined further below.

A key feature of the invention is the gradual change and the controlled, shorter length of the transition section between the soft, flexible portion and the stiff portion of the tube. Another key feature of some aspects of the invention is the "wedged-in" construction in the transition section 19 of the catheter where a layer of one material forms a wedge-shaped profile extending into another material. This construction is naturally formed provided that the "skewing volume", (defined hereinafter) is not overly short, and the viscosity of the "wedging" material or resin is not overly high when compared with the resin into which it is "wedged". As will be more clearly explained hereinafter, in the co-extrusion process, the speed of flow of the resin is usually the greatest near the center of any flow channel of the co-extrusion head and slowest near the walls of the flow channel. Therefore, any new and different material introduced into one flow channel tends to flow out first near the center of the channel and last near the walls, thus forming the "wedged-in" structure. Another way of forming a "wedged-in" construction is to introduce an interior layer at a gradually increasing rate.

In practicing the invention, one material or resin is always gradually combined with another material in the transition section 19, in some aspects of the invention forming a "wedge" structure. The "wedge" can be in the form of a gradually thinning layer, as shown in FIG. 1A, or in other gradually changing shapes, such as multiple spear points. As previously mentioned, this wedge construction forms an extremely secure, virtually unbreakable joinder between two resins because of the large surface contact area created between the two resins which effectively restricts relative movement between them.

The invention is illustrated in connection with examples of catheters that have differential stiffness because of the use of different materials or resins. FIG. 1A shows a catheter in which the proximal section 18 is of a single layer of material that makes the section 18 stiff. The distal section 16 is also of a single layer of soft material that makes the distal section 16 soft and flexible. In the transition section 19 the stiff material of the proximal section 18 is wedged into the soft material of the distal section 16, thus providing an enclosed, secure joinder of the stiff and soft materials and avoiding an abrupt change in material that can cause kinking.

FIG. 1B shows a catheter in which the stiff material of the proximal section 18 is an inside layer 15 with the soft material of the distal section 16 forming an outside layer 11 along the proximal section 18 as well as the transition section 19. As in the embodiment of FIG. 1A, the stiff material is wedged into the soft material in the transition section 19.

In FIG. 1C, the construction of the catheter is similar to that of the embodiment of FIG. 1B except the stiff material also extends into the distal section 16 to form a thin inside layer 13 with the soft material forming the outside layer 11 as in the embodiment of FIG. 1B.

FIG. 1D shows a catheter construction in which the stiff material of the proximal section 18 forms an interior layer 17, and the stiff material extends into the transition section 19 and is wedged into the soft material of the transition section 19. However, in this embodiment, the outside layer 11 is uninterrupted and extends the entire length of the tubing from the proximal section 18 through the transition section 19 and the distal section 16. Also, in this embodiment of FIG. 1D, the inside layer 13 is of a different material from the material of either the outside layer 11 or the interior layer 17, layer 11 being of a material that is softer than the stiff material but suitable for movement of a guide-wire.

FIG. 1E shows a catheter construction in which a plurality of materials of different stiffness provide a differential stiffness catheter. The stiffest material of the proximal section 18 forms an interior layer 15, and the stiffest material extends into the transition section 19 and is wedged into the less stiff material in portion 19c of transition section 19. This less stiff material, in turn, is wedged into a softer material in portion 19b of transition section 19, which, in turn, is wedged into the softest material in portion 19a of transition section 19. Thus, in this embodiment, four materials of different stiffness provide the differential stiffness along the length of the catheter. However, three or more than four materials may also provide a similar construction. In this embodiment, both the outside layer 11 and the inside layer 15 are uninterrupted and extend the entire length of the tubing from the proximal section 18 through the transition section 19 and the distal section 16. In the embodiment of FIG. 1E, the four different materials are successively wedged into one another in such a way that portions 19a, 19b and 19c of transition section 19 overlap and three materials are present in each area of overlapping portions. Alternatively, portions 19a, 19b and 19c may be immediately adjacent to or separated from one another within transition section 19 to provide differential stiffness for the catheter.

FIG. 1F illustrates a non-wedged construction in which the stiff material and the soft material both extend the full length of the catheter, the differential stiffness resulting from a change in relative thickness of the two materials which takes place in the transition section. The stiff material forms an inside layer 15 which is significantly thicker in the proximal section 18 than in the distal section 16, gradually decreasing in thickness in transition section 19. The soft material forms an outside layer 11 which is significantly thinner in the proximal section 18 than in the distal section 16, gradually increasing in thickness in the transition section 19. Thus inner layer 15 provides a continuous smooth surface for passage of a guidewire, while outer layer 11 provides a low-friction layer for passage of the catheter through bodily passages. Typically, transition section 19 in such a catheter is about 0.25 to 20 inches long. In alternate embodiments, either inner layer 15 or outer layer 11 may not extend the entire length of the catheter; that is, inner layer 15 may terminate anywhere along the length of proximal section 18 or outer layer 11 may terminate anywhere along the length of distal section 16. Typically, however, either inner layer 15 or outer layer 11 or both extend the entire length of the catheter. Alternatively, three or more materials may extend along the length of the catheter in a non-wedged construction. For example, a third material may provide an interior layer of intermediate stiffness between the stiffer layer and the softer layer. This interior layer provides a relatively thick lengthwise layer segment in transition section 19 between the thicker stiff layer of proximal section 18 and the thicker soft layer of distal section 16, gradually decreasing in thickness in the proximal and distal sections.

Generally, as used herein, the term "transition section" is known in the art, and refers to the portion of the catheter in which the properties of the tubing change from those principally provided by one material, i.e., the primary material of the distal section (distal primary material) to those principally provided by another material, i.e., the primary material of the proximal section (proximal primary material). Along the length of the tubing, the volume percent of the proximal primary material changes from a maximum in the proximal section to a minimum in the distal section, while the reverse is true for the distal primary material. The transition section, therefore, may be defined relative to this maximum volume % of the proximal primary material (Vmax). That is, as used herein, the term "transition section" is defined as the portion of the tubing between two points along the length of the tubing. The proximal primary material at the proximal end point of the transition section is at least about 95% of the Vmax, while the proximal primary material at the distal end point of the transition section is no more than about 5% of the Vmax. Thus, for the simple catheter tubing of FIG. 1A, the Vmax is 100%, and the transition section is the portion between about 95% (95% of 100%) and about 5% (5% of 100%) by volume of the proximal primary material. In FIG. 1D, the outside layer of the distal primary material carried throughout the length of the tubing does not affect the definition of the transition layer, i.e., if the Vmax (of the proximal primary material) is 80%, the transition section is the portion between about 76% (95% of 80%) and about 4% (5% of 80%) by volume of the proximal primary material. In FIG. 1C the proximal primary material is carried into the distal section as an inside layer throughout the catheter tube. Therefore, for the purpose of determining the transition section boundaries, this layer may be treated as a separate material not part of the Vmax. Thus, if the true volume % of the proximal primary material in the proximal section is 95% but the inside layer alone is 5%, then the Vmax is about 90%, and the transition section is the portion between about 85.5% (95% of 90%) and about 4.5% (5% of 90%) by volume of the proximal primary material.

As previously indicated in describing the background of the invention, the primary difficulty encountered in co-extrusion of differential stiffness tubing as taught by the prior art is the length of the transition section 19. As will be evident from further description of the invention, there are a number of design aspects of the prior art co-extrusion heads and systems that result in these undesirable long transition sections.

Figure 2:
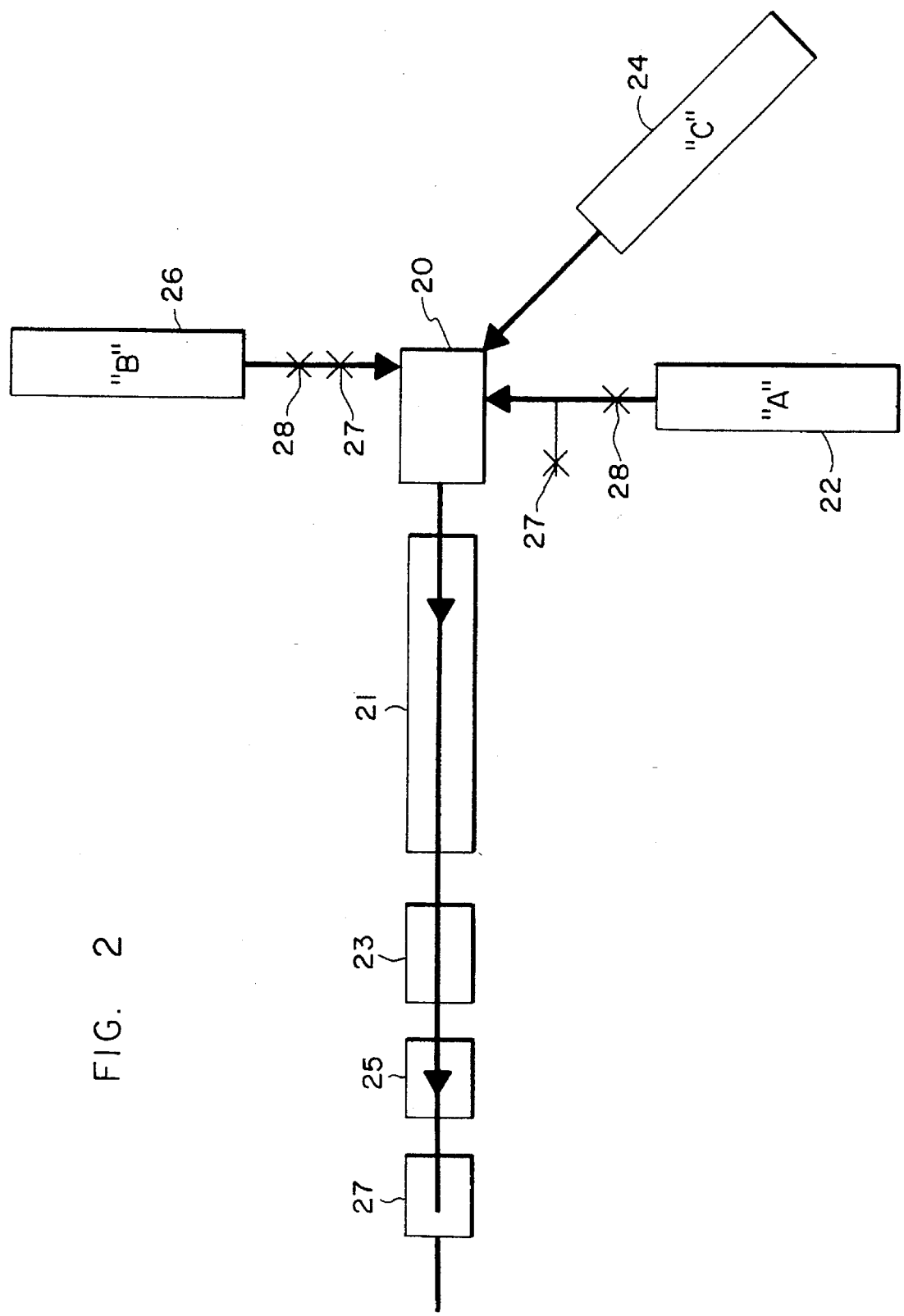
FIG. 2 is a schematic diagram of a system for producing a differential stiffness catheter using the co-extrusion technique of the invention.
Figure 5:
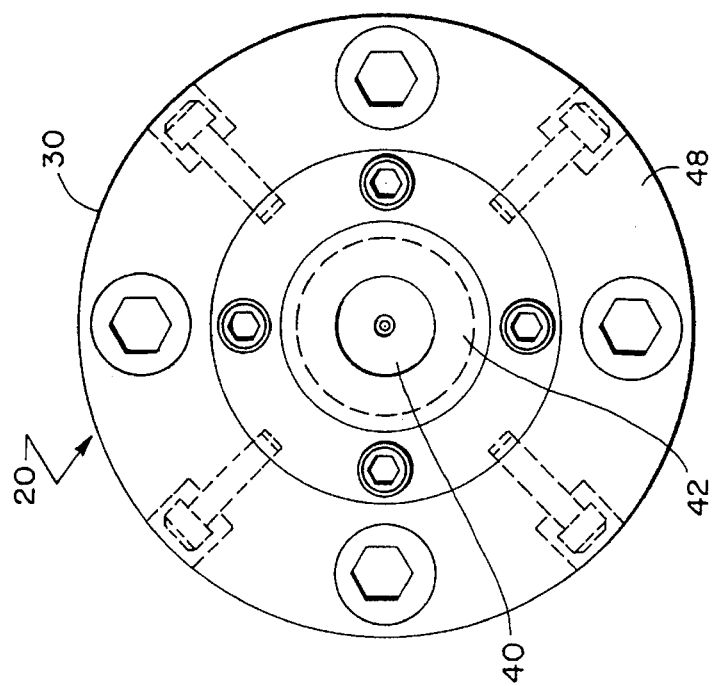
FIG. 5 is an end view of the co-extrusion head of FIG. 4.
Figure 3A:
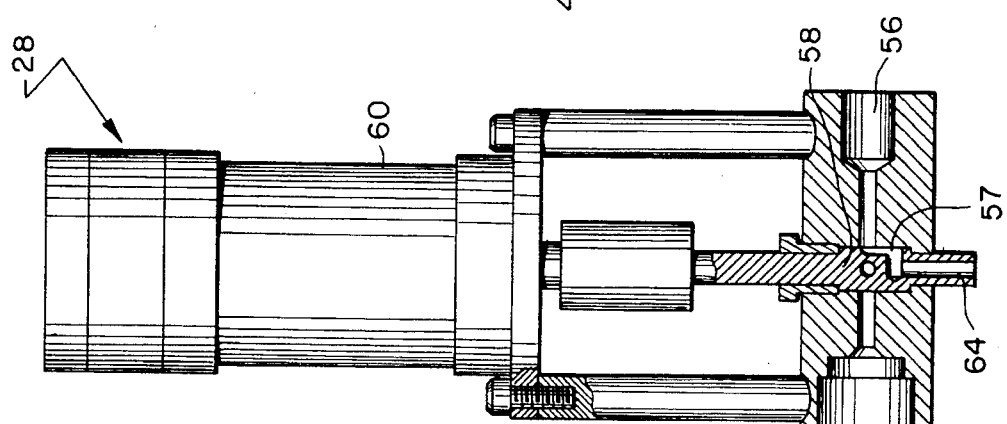
FIGS. 3A and 3B are views, partly in section, of a two-stage flow modulator used in the system of the invention, FIG. 3A being a front elevational view and FIG. 3B being an end elevational view.
Figure 3B:
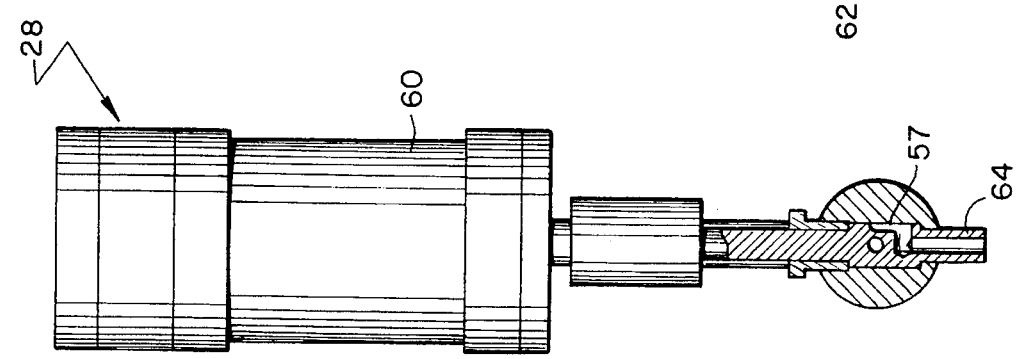

Referring now to FIG. 2, there is shown schematically a system for co-extruding differential stiffness tubing, such as catheters. The system includes a co-extrusion head indicated, generally, by the reference numeral 20 into which extruders 22, 24 and 26 feed the different resins, such as a soft resin and a stiff resin, that will be used to form the finished tubing. For purposes of illustration, extruder 22 provides a resinous stream for a resin "A" which, for example, will ultimately form the outside layer 11 of the catheter of FIG. 1D, while extruder 26 provides a stream of resin "B" that will form the interior layer 17 of the finished catheter. Similarly, extruder 24 provides a resinous stream for resin "C" which is the material that will form the inside layer 13 of the finished catheter. As illustrated in FIGS. 3A and 3B, and as more fully described hereinafter, a modulating device, indicated generally by the reference numeral 28, regulates the flow of the resins from each of the extruders 22 and 26 into the co-extrusion head 20, while another modulator 27 may be used to bleed resin "A" from the head 20 to relieve residual pressure. To produce catheter tubing with differential stiffness, the modulators 28 are actuated periodically and in synchronized fashion to abruptly stop or change the resin flow to the head 20. Because of the design of co-extrusion head 20, the interface between the stiff resin and soft resin is naturally sheared and elongated when flowing through the flow channels of the head 20. Thus, these abrupt changes or stop-pages by the modulators 28 result in a very gradual change of stiff layer thickness in the tubing, creating the gradual stiffness change and resulting in the wedge structure in the transition section 19 of the catheter tubing. After discharge from the head 20, the tubing is cooled by passage through a water tank 21, a laser mike 23, puller 25 and cutter 27 to form the catheter tubing.

Figure 4:
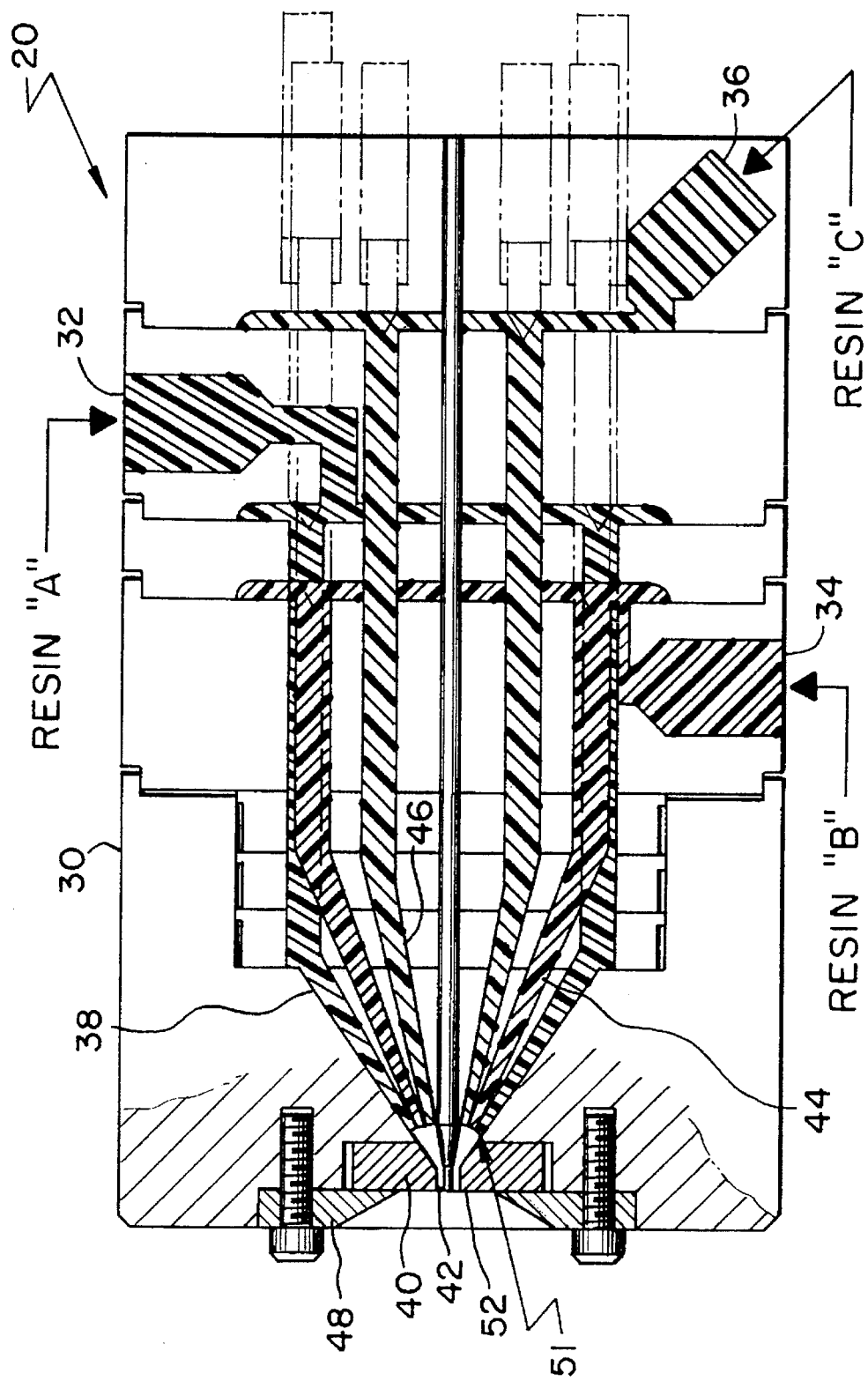
FIG. 4 is a side elevational view partly in cross-section illustrating a three-layer co-extrusion head utilizing the principles of the invention.
Figure 6:
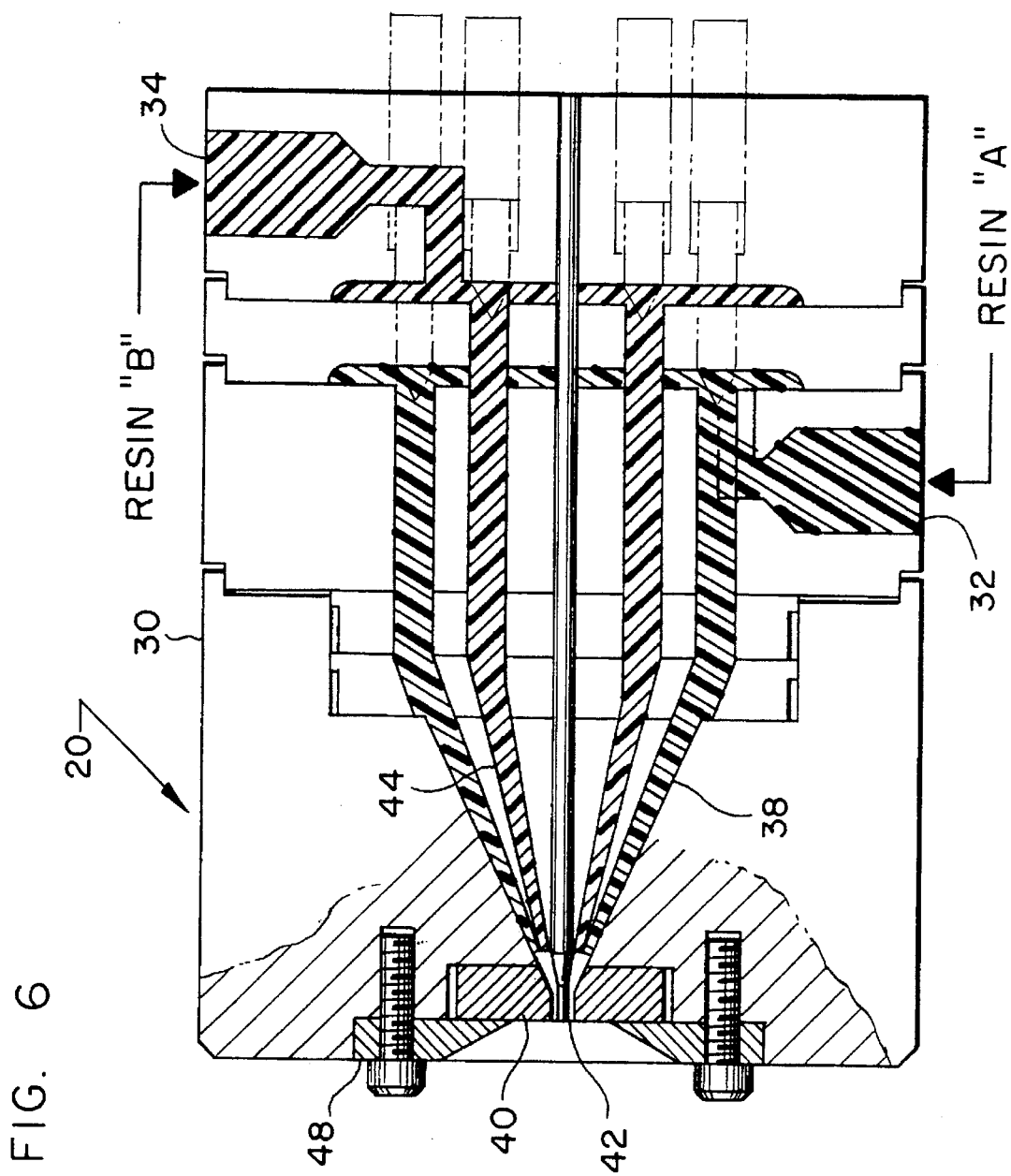
FIG. 6 is side elevational view partly in cross-section similar to FIG. 4 but showing a two-layer co-extrusion head.

As is well known to those skilled in the art, a co-extrusion head is an assembly of many precision machined parts that provide a plurality of flow channels, each of which is connected to one of the extruders. FIG. 4 illustrates the design of a co-extrusion head 20 for producing a tubing of three different materials, such as that shown in FIG. 1D. FIG. 6 illustrates a head design for producing a tubing of two different materials, such as the tubing illustrated in FIGS. 1A, 1B and 1C. The co-extrusion head 20 has a main body 30, usually of a cylindrical shape, in which is formed an inlet 32 for resin "A", an inlet 34 for resin "B" and an inlet 36 for resin "C". Each of the inlets is connected to the respective one of the extruders 22, 24 and 26, and through a flow channel formed in the main body 30, to a die 40 which, together with the tip 42, forms the exit from the head 20 for the flow of resins to create the desired configuration of the finished product. As illustrated in FIG. 4, the co-extrusion head 20 has a flow channel 38 connected to inlet 32 for resin "A", a flow channel 44 that is connected to inlet 34 for resin "B" and a flow channel 46 that is connected to inlet 36 for resin "C". A removable cap 48 on main body 30 provides access to the head to change the die 40 and tip 42. It is not an unusual situation that a producer of medical tubing such as catheters will frequently change the die 40 and tip 42 without changing the entire co-extrusion head 20 in order to produce tubing of different sizes or of different materials. This change sometimes can take place several times a day. To accommodate this need, the design of the head 20 can be such so as to include in the same co-extrusion head 20 both large and small dies 40 and tips 42.

When used herein, a "side stream" means any resinous stream in the co-extrusion head 20 of the type of FIG. 4 that is either on the outside or on the inside at point 51 where the resinous streams meet prior to exiting the head 20 at point 52. Similarly, "interior stream" is any resinous stream in the co-extrusion head 20 that is between two side streams at point 51.

"Contact volume" of any resin, such as resin "C", is the volume in the flow channel portions of the co-extrusion head 20 where resin "C" is flowing jointly with at least one other resin, such as resin "B", and where resin "C" is in intimate contact with solid non-moving surfaces of the head 20 in the section where there is such joint flow. Also, the term "contact surface" means the solid, non-moving surface of head 20 with which resin "C" is in intimate contact in the "contact volume". In FIG. 4, contact volume for resin "C", as well as resin "A", is the volume in the flow channel between point 51 and exit point 52. Contact volume for resin "B" is zero, since it does not contact any solid surface after it passes point 51.

Also, by definition, the "residual flow volume of a resin" is the volume of a flow channel section between the discharge from the modulator 28 and the point where the resin joins another resinous flow for the first time.

The "skewing volume" of a resin is the volume in a flow channel between the point where the resin stream "C" joins another flow stream for the first time (the start of the contact volume) and the point where the resin exits from the co-extrusion head 20. In the typical co-extrusion head example of FIG. 4, the "skewing volume" of all three resins is the volume in a flow channel between point 51 and the resin exit point 52.

As previously indicated, the contact volume and the skewing volume are probably the most influential factors in forming the length of the transition section. The lower the volumes, the shorter the transition section that will be formed. The undesirable lengthy transition section occurs in prior art co-extrusion heads because the solid contact surface drastically slows down the resin flowing by it to cause a "drag-out" effect that overly elongates the resin interface. For the shortest transition section, zero contact volume should be designed into the co-extrusion head 20 since zero contact volume design completely or substantially eliminates the drag-out effect of the interruptable resin "B", and as a result, this design will produce the shortest transition sections possible when the flow of resin "B" is interrupted. However, as a practical matter, for resin "A", FIG. 4 illustrates a flow channel arrangement in a co-extrusion head design that we have termed a "die-length contact volume" head design. With this design of FIG. 4, the contact volume is no greater than the volume covered by the length of the die 40 multiplied by a factor of 10, and is no less than the volume covered by the die length. Preferably, the contact volume is equal to the volume covered by the die length. This "die length contact volume" head design is especially useful in interrupted side streams in co-extrusion rather than where the center streams are interrupted, and in some designs, the use of a die is deemed necessary to control the overall tube concentricity and assure its uniformity. As a practical matter, in many cases the contact volume should not exceed the volume contained in the desired transition section length multiplied by a factor of 10. For producing some catheters of a small diameter, the contact volume can be as small as 0.5 ml. Thus, by the die-length contact volume design of the co-extrusion head 20 as shown in FIG. 4 for resin "A", one of the most influential causes of lengthy transition sections is practically eliminated.

Also, it is desirable to keep the discharge opening of the flow channel 44 for resin "B" as small as possible where it joins the flow channel 38 for resin "A". As previously described, the design of the head 20 shown in FIG. 4 uses a die-length contact volume for resin "A", and by changing the thickness of the die 40, the contact volume can be varied.

The length of the transition section also can be changed by a simple change of tooling in the tip 42 and die 40 of the head 20. By changing this tooling, both the skewing volume for resins "A" and "B" and the contact volume for resin "A" can be modified.

However, there are other factors that influence the length of the transition section 19 in a differential stiffness catheter. One factor that influences the length of the transition section is the final cross-sectional area of the tubing to be formed. Tension and internal air pressure are applied, as is known in the art, to the hot, as-extruded tubing exiting the extrusion head, resulting in elongation and shaping of the tubing to preselected inside and outside diameters. The length of the transition section is inversely proportional to the final cross-sectional area of the wall of the tubing. In other words, thin tubing with very small diameters tend to have very long transition sections.

As is well known to those skilled in the art, in any continuous extrusion process, when the resin flow to the extrusion head is suddenly shut off, a small amount of resin will continue to flow for some time, even for minutes in some instances. Theoretically, this "residual flow" effect on the interrupted resin stream "B" will therefore cause a lengthy transition section. However, we have determined that the amount of residual flow decreases with a decrease in the residual flow volume previously defined herein. Therefore, by keeping residual flow volume small, the effect of residual flow can be minimized. Another way to reduce the residual flow effect is through the use of modulators.

Figure 7:
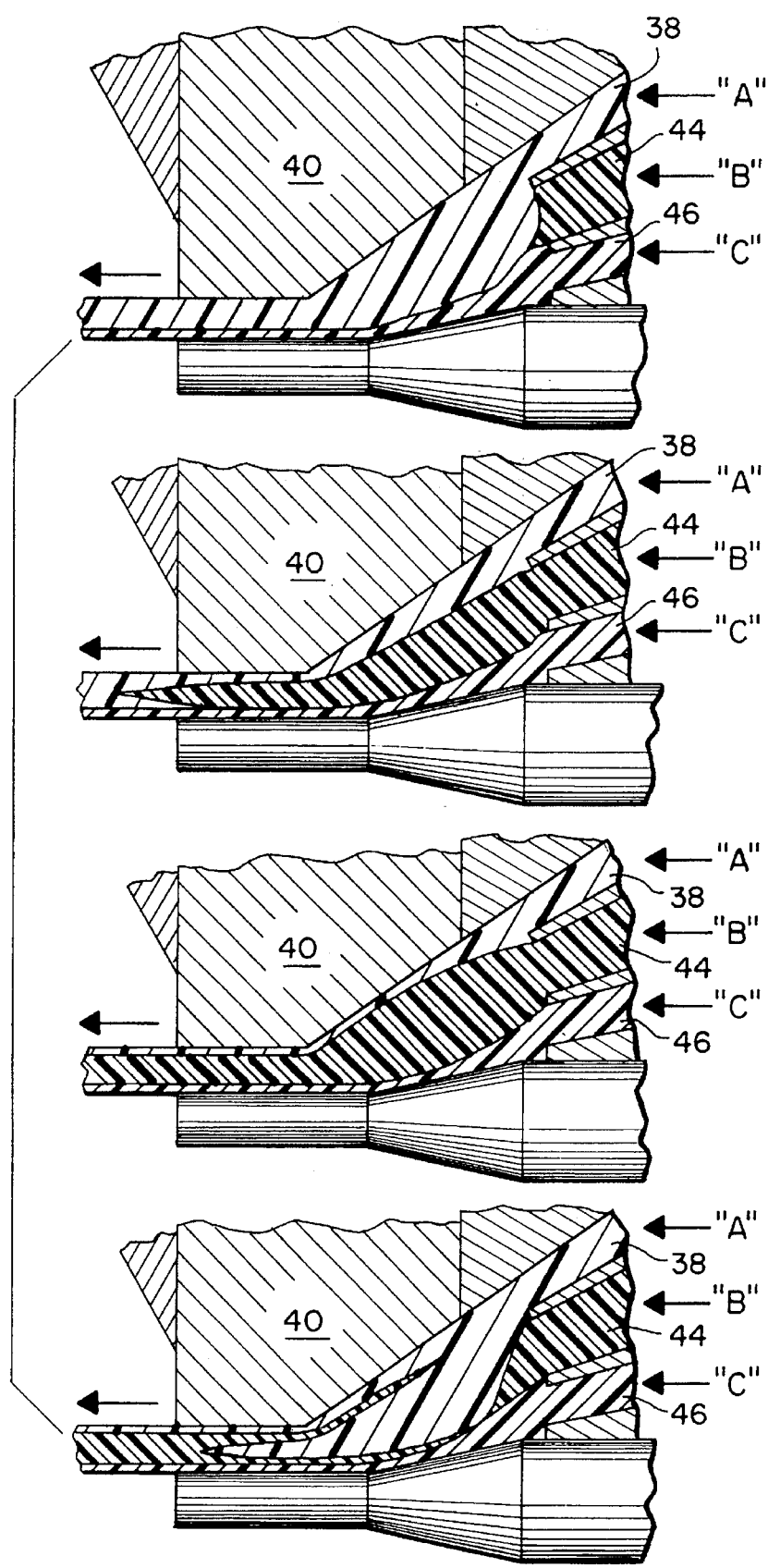
FIG. 7 is a series of diagrams showing the steps of a process performed using the principles of the invention.

As is well known to those skilled in the art, after a resin stream, such as resin "B" is introduced into a stream of resin "A" as illustrated in FIG. 7, the shape of the resin stream "B" changes as it flows downwardly, and this results in a longer transition section. The reason for this phenomenon is that fluids flow faster at the center of a stream than at the sides, and therefore, the further the fluid flows, the more "skewed" becomes the stream. In the case of the flow of resin "B", this results in a longer transition section. Therefore, by keeping the skewing volume to a minimum, preferably below the resin volume contained in the desired transition section multiplied by a factor of 10, the length of the transition section can also be kept to a minimum.

The length of the transition section can also be changed by changing the viscosity of the resins. For example, when the leading edge of the stiff layer is used to wedge into the layer of softer material as illustrated in FIGS. 1A, 1B, 1C, 1D and 1E, raising the viscosity of the stiff layer or lowering the viscosity of the softer side layers will shorten the length of the transition section.

Figure 8A:
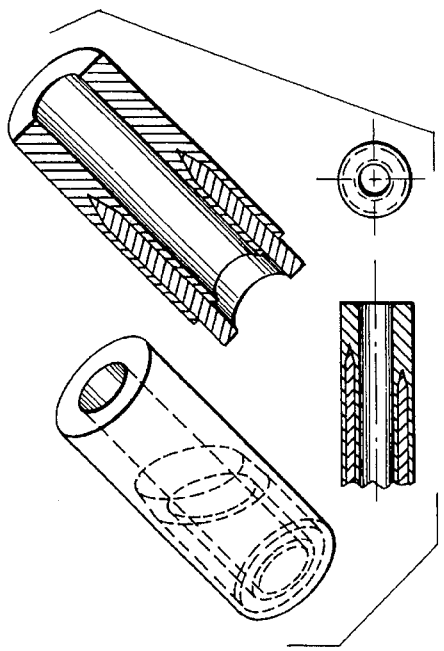
FIGS. 8A, 8B and 8C each contain various views of a section of a catheter to illustrate the differences between a slanted end and an even end, and the configuration normally found in an even end.
Figure 8B:
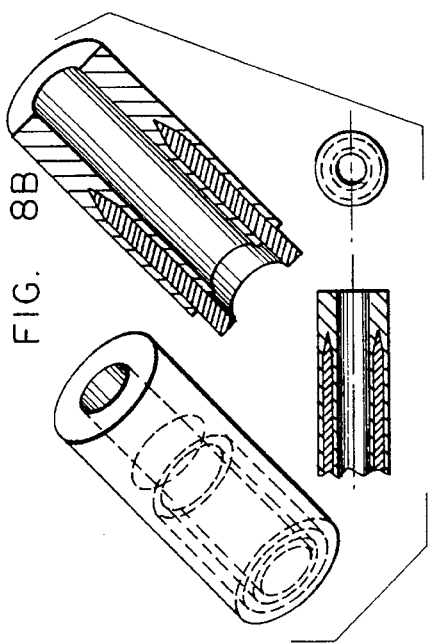
Figure 8C:
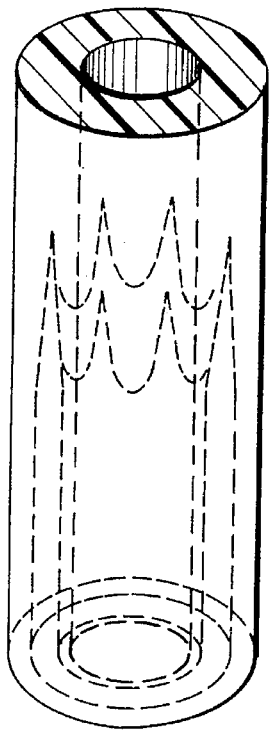

Note that from the design of the flow channels in the head 20 as illustrated in FIGS. 4 and 6, all of the foregoing factors have been designed into the head 20 so as to result in keeping the transition section 19 to a desired short length. Another important feature of the head 20 of the invention is the use of means to adjust the "slanting" of the "wedge" of the stiff layer. In FIGS. 4 and 6 the head design includes adjustment screws 54 on the rear of the head 20. By adjusting the screws 54, the length of the annular stiff layer, and thus the length of the transition section 19, can be varied along only a portion of the annular layer to produce a slanted end, as illustrated in FIG. 8A. FIG. 8B shows the stiff layer of uniform length around the entire circumference to produce an "even" wedge. In FIGS. 8A and 8B, the tubings are shown schematically; in particular, the downstream, thinner ends of the wedges of the stiff layers are shown as sharp edged and smooth. In the actual product produced by the process described above, however, the downstream edge of the wedged-in layer ends in a plurality of longitudinally extending "spear points" of one material extending into the other in the wall of the transition section, as shown in FIG. 8C. (In the tubing of FIGS. 8A–8C, points of the stiffer material extend into the softer material.) The downstream ends of the points are circumferentially spaced apart in the wall of the transition section, and the points gradually increase in size in the upstream direction until they join to form the annular layer shown in FIGS. 8A–8C.

Also, as is evident to those skilled in the art that in making tubing for catheter applications, it is very important to have precise control over the inside and outside diameters of the tubing as well as the wall thicknesses. In any tube extrusion process, some variation in tube diameter (either interior or outside diameter) always occurs if the total resin flow rate is changed. The variations in diameter also occur when total resin flow is reduced due to the interruption of one or more resin streams in co-extrusion processes. The extent of the diameter change increases with the increased percentage of the stream of the interruptable resin relative to the total resin flow. Therefore, too sudden an interruption, although good for producing short transition sections, can sometimes produce too sudden a change in the diameter of the tubing and result in undesirable ripples. Also, because there is always a lag between interruption induced diameter change and the transition section of a tube, this lag distance can be as short as a fraction of an inch or as long as many feet. The lag distance increases with the increase of skewing volume and it is inversely proportional to the final cross-sectional area of the tubing.

An important design feature of the invention is that the co-extrusion head 20 of the invention has no moving parts, thus assuring that the diameter of the tubing will be consistently accurate which is especially important for medical tubing such as catheters. Also important in maintaining consistent diameters of the tubing is the close match of melt strengths of the resins used.

Although most of the emphasis in the system of the invention has been on the design of the co-extrusion head 20 in order to produce tubing of a consistent diameter and having a transition section of a desired short length, the modulator 28 is also important in order to regulate and control the actual length of the transition section as well as the profile for any particular tubing. The modulator 28 functions to regulate the flow rate of the resins in a rapid and precise fashion. A typical modulator 28 is illustrated in FIGS. 3A and 3B, which show a two-stage type modulator in which the flow can be regulated so as to flow through to the head 20 or interrupted to direct the resin flow to a recycling container (not shown). The modulator 28 must be fast acting so as to operate to change the flow within no more than two seconds and preferably in less than 0.5 seconds. The modulator 28 thus has an inlet 56 leading to a chamber 57 into which extends a valve member 58 operated by actuator 60. Depending upon the position of valve member 58, the resin flowing into the chamber 57 is directed to the outlet 62 which is connected to the head 20 or the resin is directed into a bypass outlet 64. A variety of different designs of the modulating device 28 can be utilized as long as they have extremely fast responses and can produce rather precise flow controls. Since a typical cycle for making one length of tubing for a single catheter is only about 0.5 to 10 seconds, rapid response is extremely necessary. If desired, the modulator 28 can be replaced by a plunger type modulating device, actuated by a servo valve with a programmer (not shown). The programmer may be of any suitable design such as that marketed by "Moog" Electronics and Systems Division which produces and markets a line of parison programming systems.

It should be noted that if the co-extrusion head 20 is properly designed and operated, rather simple on-off types of modulating devices may be sufficient, depending upon the type of tubing being produced. Also, devices with mechanical gradual flow reduction or gradual flow-increase functions can also be used depending upon the tubing requirements.

Although modulators may be programmed to deliver tubing having a consistent diameter throughout the production cycle, small variations do occur due to slight mismatches of the modulators. A tubing can be produced with the most consistent diameter, e.g., for use as a catheter (before tapering) by keeping the skewing volume greater than the resin volume contained in distal section 16 of the catheter, and preferably greater than the resin volume of the distal section multiplied by a factor of 5.

In FIG. 7 there is illustrated the operating steps of a complete cycle for producing the differential stiffness catheter of FIG. 1D. This figure shows schematically the die 40 and tip 42 of the head 20 and illustrates the flow of the resins through the die 40 and tip 42. In the first phase, the flow of resin "B" is stopped while the flow of resins "A" and "C" are on. This forms the soft distal section 16 from resin "A" with a thin inside layer 13 formed of the material of resin "C". The flow of resin "B" is then commenced while the rate of flow of resin "A" is reduced and the flow of resin "C" continues. In this phase, the transition section 19 is formed. In the third phase, the flow of all three resins is on to form the stiff, multi-layered proximal section 18. In the last phase, the flow of resin "B" is stopped and the rate of flow of resin "A" is increased to purge out resin "B". The cycle is then repeated starting with the first phase. Note that in all phases the flow of resin "C" is continuous and at a constant rate. This illustration of a complete cycle of a process performed according to the principles of the invention shows that the process extrudes different resins sequentially as well as simultaneously. Prior art processes teach only simple co-extrusion in which different resins are extruded simultaneously only.

Although in many cases of differential stiffness tubing only one stiff resin will follow one soft resin in a consecutive manner, there are applications in which three or four resins of different stiffness are co-extruded consecutively to produce a finished product with improved kink-resistance, and with such a process, better control of tubing diameters can be achieved.

The head and systems designs of the invention are also useful where it is desired to obtain a specified diameter and wall thickness and to combine interrupted resin streams technology with tapering and lumen air regulating techniques. When so doing, the timing of all these devices should be synchronized to avoid drift.

It is also known to those skilled in the art that in co-extruded products, a side layer of non-sticking, non-compatible material can be removed in a post-extrusion operation resulting in a product with one less layer. When this technique is used on tubing made with the methods and systems described herein, this technique can be beneficial in reducing diameter fluctuations due to resin melt strength differences as well as other reasons.

There are some applications where it is desirable to increase the transition section in a medical tube, such as a catheter. The obvious remedy is to use the modulating device 28 to lengthen the transition section. However, as previously described, it is also possible to increase the contact volume and/or the skewing volume in order to lengthen this transition section.

Figure 12A:
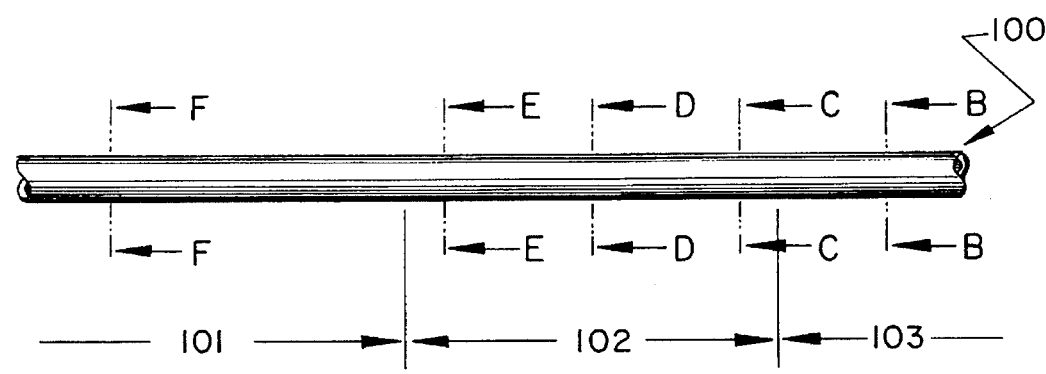
FIGS. 12A–12F show a multi-lumen catheter tubing produced using the principles of the invention.
Figure 12B:
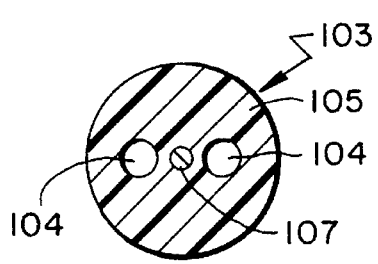
Figure 12C:
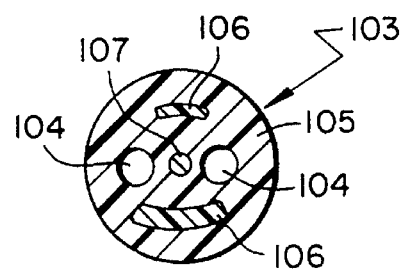
Figure 12D:
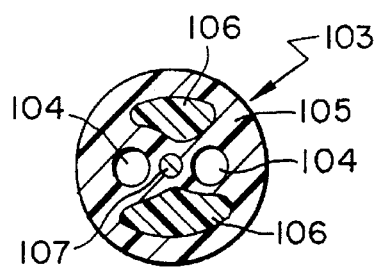
Figure 12E:
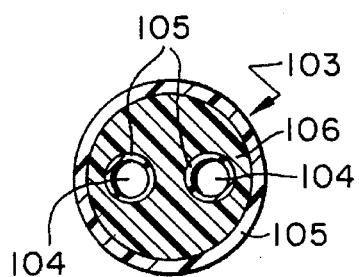
Figure 12F:
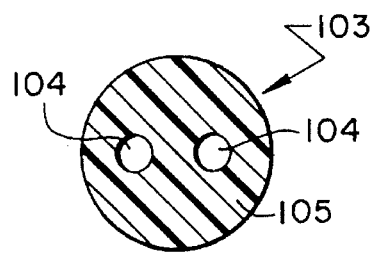

From the foregoing description it will be evident that we have described a new technology for making tubing, especially medical tubing for such applications as variable stiffness catheters, soft tip catheters, etc. However, multi-lumen catheters can also be made using the principles of the invention. A typical multi-lumen tubing for such a catheter is shown in FIGS. 12A–12F. In FIG. 12A, tubing 100 includes stiffer proximal section 101, transition section 102, and softer distal section 103. FIG. 12B illustrates a cross section of softer distal section 103 taken along line B—B of FIG. 12A. In FIG. 12B, distal section 103 includes lumens 104 formed within softer material 105. FIGS. 12C–12E illustrate cross sections of transition section 102 taken along line C—C, D—D, and E—E, respectively, of FIG. 12A. In FIG. 12C, the portion of transition section 102 near distal section 103 includes lumens 104 formed within softer material 105, with inserts of stiffer material 106 on either side of lumens 104. FIG. 12D, from near the center of transition section 102, is similar to FIG. 12C, but with larger insertions of stiffer material 106. In FIG. 12E, the portion of transition section 102 near proximal section 101 is made up largely of stiffer material 106, with thin layers of softer material 105 adjacent lumens 104 and the outer surface of transition section 103. In FIG. 12F, proximal section 101 includes only stiffer material 106, with lumens 104 formed therewithin. Typically, when a plurality of stiffer sections (each of which may form one or two proximal sections 101) and softer sections (each of which may form one or two distal sections 103) are extruded, a small remnant of stiffer material remains at the core of the softer and transition sections between stiffer sections. Such a remnant is shown in FIGS. 12B, 12C, and 12D as remnant 107 of stiffer material 106.

Alternatively, the multi-lumen catheter may include three or more lumens, and the lumens may have any of a variety of shapes and may be of the same or different shapes and sizes. Such multi-lumen tubing is useful for applications in which known multi-lumen tubing has been found useful, for example, in balloon catheters or electrophysiology (EP) catheters. A particular advantage is provided by the variable stiffness tubing in an EP catheter. When the distal tip of the EP catheter is deflected for maneuvering of the catheter through tortuous anatomies, the short transition section and soft distal section permit faster recovery of the straight-line axial configuration than has been achieved in prior art EP catheters.

Also, in addition to the two and three resin systems described herein, more than three resin systems can be made, such as for channel balloon concepts and for some multi-lumen concepts. It should also be pointed out that the differential stiffness tubing made according to the invention not only can be used for making the full length of the catheter, they can also be used to make only a part of the catheter. For example, the invention can be used to make a single lumen tubing inside the balloon, or produce a catheter with the distal section combined with a proximal section formed of either a braided construction or a metal tubing such as Nitenol tubing. Another type of catheter construction to which the principles of the invention can be applied is to produce a catheter with a low friction layer on the inside surface for good guidewire movement.

Figure 13:
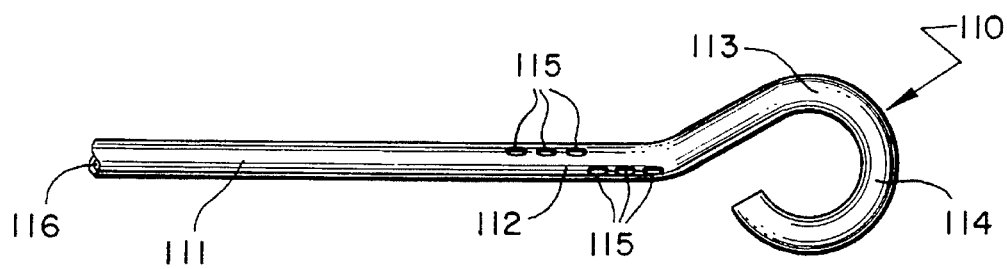
FIG. 13 is an angiographic catheter produced using the principles of the invention.

In yet another type of catheter construction, the catheter distal section may be shaped, e.g., by heating to form a bent configuration in its relaxed state. For example, a J-tip or hook-shaped profile may be formed at the distal tip of the catheter. The wall of this bent or other catheter may be perforated by known means, e.g., at the proximal section to provide for inflation of a balloon via the central passageway or at the transition or distal section to provide for dispensing of fluid medication or a fluoroscopic dye. An example of such a catheter is shown in FIG. 13, showing angiographic catheter 110 having proximal section 111, transition section 112, and distal section 113. Distal section 113 has been, e.g., heated and bent to form loop 114 in its relaxed configuration. In use, catheter 110 is threaded onto a guidewire (not shown), which holds distal section 113 in a configuration generally coaxial with the guidewire. When the distal section 113 is in position within a bodily passage, the guidewire may be partially withdrawn to permit distal section 113 to form loop 114 of its relaxed configuration, which holds catheter 110 in place. The wall of transition section 112 may be perforated to provide apertures 115 for fluid communication between central passageway 116 of catheter 110 and the outside of the catheter. Apertures 115 may be used for, e.g., the dispensing of a dye for fluoroscopic viewing of the bodily passage.

Figure 14:
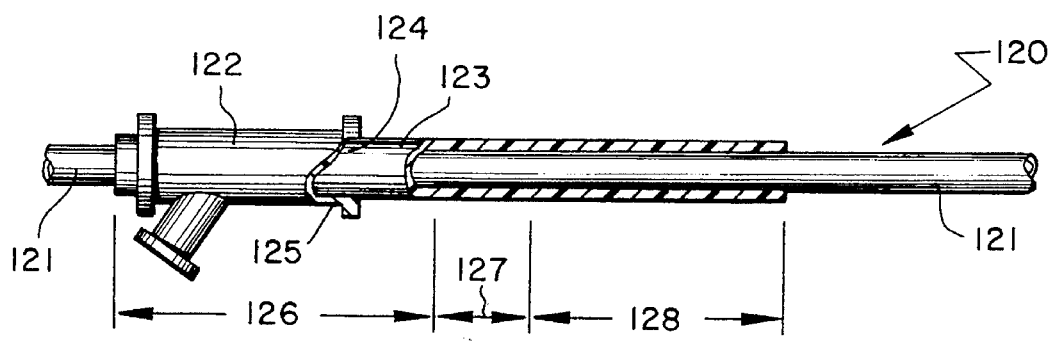
FIG. 14 is a strain relief joint including tubing produced using the principles of the invention.

In addition to differential stiffness catheters, the invention can be employed to produce soft-tip catheters, catheters of varied colors and for "strain-relief" of any part of a catheter. In the last mentioned case, a short differential stiffness section of the catheter is formed at the proximal end to provide a transition from the connector, for example, to which the tubing is attached and the main portion of the proximal end of the catheter. Alternatively, a separate short piece of differential stiffness tubing can be used to provide improved strain relief to a known tubing/connector assembly. A strain relief insert of this type is shown in FIG. 14. Catheter 120 of FIG. 14 includes flexible shaft 121 and rigid fitting 122 coaxial with shaft 121, shaft 121 extending proximally and distally from fitting 122. Tubular strain relief insert 123, which is a length of differential stiffness tubing, jackets flexible shaft 121 in the area of joint 124 between shaft 121 and fitting 122. Portion 125 of stiff second section 126 of strain relief insert 123 is disposed between shaft 121 and fitting 122, while the remainder of second section 126, transition section 127, and soft first section 128 of insert 123 extend distally about shaft 121, providing graduated flexibility to joint 124 to prevent kinking of the joint.

Figure 15:
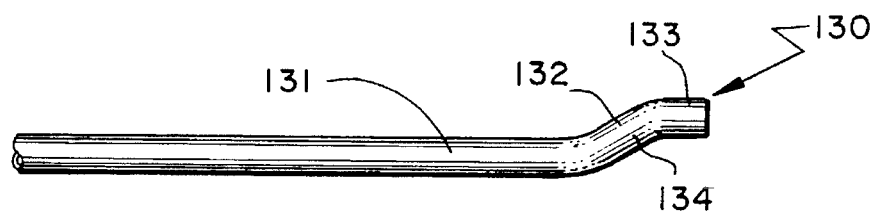
FIG. 15 is a soft tip guiding catheter produced using the principles of the invention.

A typical soft tip guiding catheter is shown in FIG. 15, in which soft tip guiding catheter 130 includes proximal section 131, transition section 132, and distal section 133. Transition section 132 has been, e.g., heat treated to form S-shaped portion 134 for maneuverability of the catheter, while short distal section 133 provides low-trauma soft tip 135 for the catheter. Typically, stiffer proximal section 131 has been reinforced with a metal braid jacket (not shown) embedded in the wall of proximal section 131. Such an embedded metal braid jacket is described further below.

Figure 10:
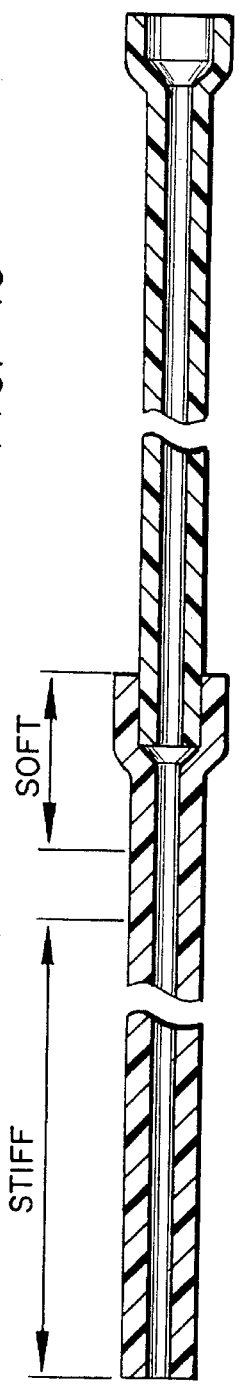
FIG. 10 is a longitudinal sectional view of another type of tubing that can be produced using the principles of the invention.
Figure 11:
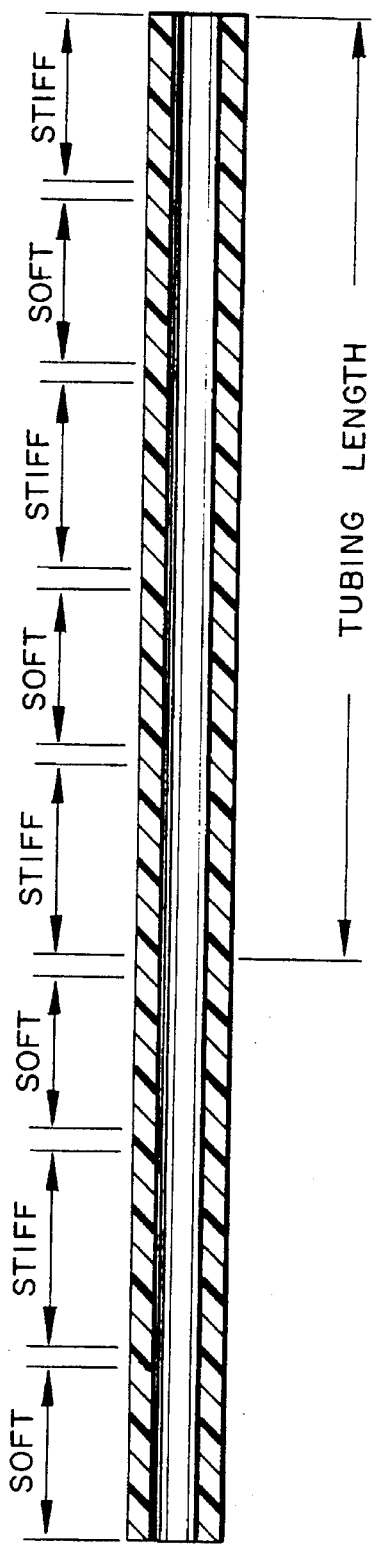
FIG. 11 is a longitudinal sectional view of still another type of tubing that can be produced using the principles of the invention.

The invention, however, is not limited to catheter products but can also be employed in producing other types of tubing and rods that require sections of varied properties. For example, FIG. 10 illustrates "bump" tubing in which the insert end is of stiffer material and the bell end is of soft material. Unlike bump tubing produced using prior art methods where both ends are soft, the stiff insert end of the tubing produced by the invention provides for a more secure and tighter fitting connection. Also, the invention can be used to produce a new tubing for quick connect fittings in which the ends are of stiff material but alternating sections are of a softer material to provide flexibility for the length of tubing between the fittings while the stiff ends are easier to fit into quick connect fittings. A tubing of this type is shown in FIG. 11. The tube includes several stiff first sections, each pair of first sections having a soft second section therebetween. Each stiff section is joined to an adjacent soft section by a transition section to form a continuous unbroken tube of differential stiffness without abrupt joints. Alternatively, only the ends of the tubing may be formed of stiff first sections, while a single long soft section may extend therebetween. The tubing of FIG. 11 may be provided in a long length for cutting at the center of any of its stiffer sections to provide a shorter length of soft, flexible tubing with stiff ends suitable for inserting into quick connect fittings.

Figure 16:
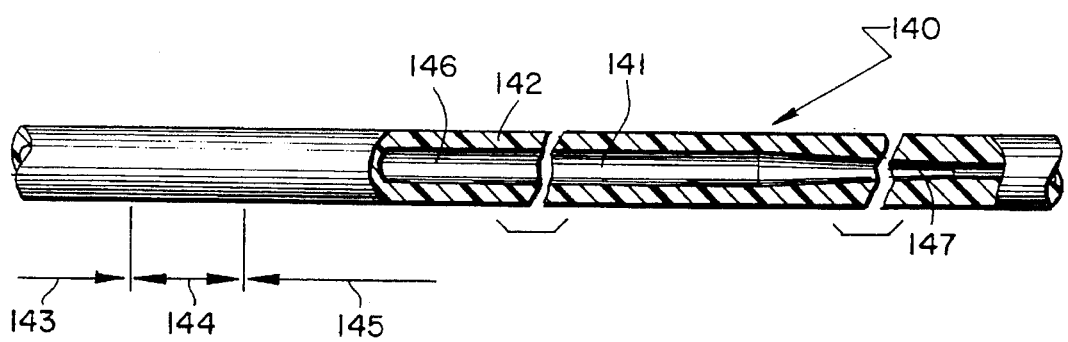
FIG. 16 is a catheter guidewire coated with tubing produced using the principles of the invention.

FIG. 16 shows another product of the invention, coated guidewire 140 for use with a medical catheter. Coated guidewire 140 includes guidewire 141 jacketed with differential stiffness tubing 142 along part or all of its length, stiffer proximal section 143, transition section 144, and softer distal section 145 of tubing 142 providing differential stiffness to coated guidewire 140. Wire 141 may be a single filament wire. Typically, guidewire 141 has proximal end 146 of uniform stiffness throughout its length and distal end 147 tapered to decrease its stiffness in the distal direction. As shown in FIG. 16, jacket 142 may be applied with increasing thickness in the distal direction to lessen the diameter difference between the wire proximal end 146 and wire distal end 145, and preferably to provide a uniform or near-uniform outer diameter along the length of guidewire 140. The differential stiffness tubing described herein also may be utilized to jacket a cable to provide differential stiffness to the cable.

In most of these applications for the invention, the main consideration in the method and systems described herein as well as the specific designs of the co-extrusion heads is the ability to make short and controlled transition sections in co-extruded tubing which have interrupted layers or elements. This technique is thus named "SCTS" technology. We have described in detail how this can be accomplished and we have also indicated the many and varied applications for a variety of different types of tubing that one may wish to produce.

The principles of the invention can be used to process a number of different materials used in making tubing. For example, nylons (polyamides), HDPE'S, polyesters, polypropylenes and other materials, including mineral and fiber-filled materials, can be used for the stiff layer or section of a tubing. For the soft layer or section, such materials as ethylene vinyl acetate, ethylenic copolymers, polyamide elastomers, polyurethanes and other thermoplastic elastomers can be used. If the tubing is for a medical catheter requiring a guidewire, many of the above listed materials for the stiff layer can be used for the inside layer that will come into contact with the guidewire, especially if the material is combined with current orientation technology to provide a low-friction surface. Also, all resins can be filled with radio opacity or not depending upon the intended use of the finished product. Moreover, in some applications for a finished product made using the invention principles, good adhesion between layers is necessary while in other applications that is not a requirement. In either case, the invention can be used.

Figure 17:
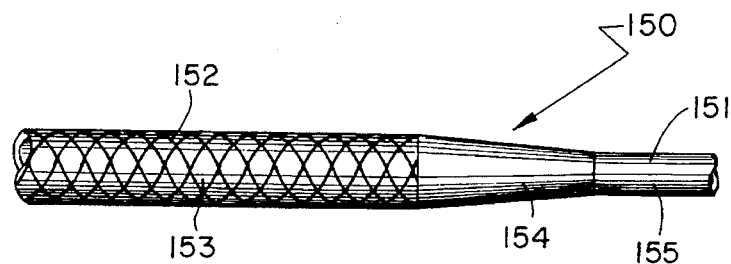
FIG. 17 is a metal braid reinforced tubing produced using the principles of the invention.
Figure 18:
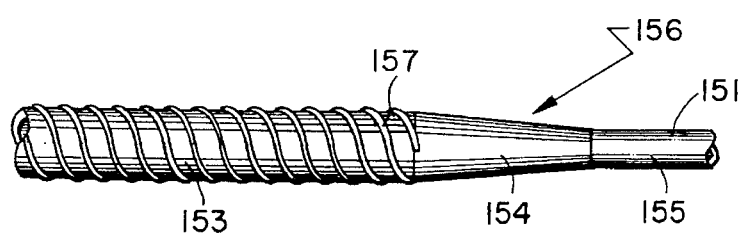
FIG. 18 is a wire wound tubing produced using the principles of the invention.

Another advantage of the invention is the versatility that it provides. Because the principles of the invention can be used to produce tubing in a continuous reel, the principles can be combined with other technologies to enhance the properties of the finished product. For example, tapering combined with lumen air control has been successfully employed to vary I.D., O.D. or wall thickness in some sections of a catheter. In particular, the invention can be used to produce microcatheters with a desired tip section having a thinner wall and smaller O.D. but with only a very slightly smaller I.D. Braiding of metal and non-metal wires can also be used with products produced by the invention to give the finished product more torqueability, higher stiffness, etc., and wire winding can be added to give additional kink resistance. Such tubings are illustrated in FIGS. 17 and 18, respectively. FIG. 17, not drawn to scale, shows metal braid reinforced tubing 150 made up of differential stiffness tubing 151 and metal mesh or braid 152 to provide a reinforcing sleeve over tubing 151. In FIG. 17, braid 152 is shown as forming a sleeve over only proximal section 153 of the tubing. Alternatively, braid 152 may extend distally from proximal section 153 to provide reinforcement to transition section 154 and, if desired, part or all of distal section 155. In FIG. 18, not drawn to scale, similar features to those shown in FIG. 17 are indicated by the same reference numerals. FIG. 18 shows wire wound tubing 156 made up of differential stiffness tubing 151 and metal wire 157 wound around tubing 151 to provide reinforcement. In FIG. 18, wire 157 is shown as being wound over only proximal section 153 of the tubing. Alternatively, wire 157 may extend distally from proximal section 153 to provide reinforcement to transition section 154 and, if desired, part or all of distal section 155. Either reinforced tubing 150 or 156 may be, e.g., heat treated to embed braid 152 or wire 157 in the outer surface of the tube wall, as shown for reinforced tubing 150.

In addition, irradiation and orientation technologies can be employed along with the invention to produce tubing of higher strength, more dimensional stability, lower elongation, etc. The latter is beneficial to prevent neck-down of catheters that results in clamping of the catheter onto the guidewire when subjected to axial stress during a medical procedure. Plastic foam technologies can also be employed with the method of the invention to produce super-soft tips.

From the foregoing description it is obvious that the number of layers, the type of layer and material used for the tubing, etc. will vary depending upon the particular characteristics desired, but it should be understood that catheters or tubes having multiple layers of a variety of materials and arranged differently than the illustrated embodiments can be formed using the principles of the invention. Although we have described the invention in connection with certain preferred embodiments thereof, it will be evident to those skilled in the art that various modifications can be made to the preferred embodiments and methods described herein without departing from the spirit and scope of the invention. It is our intention however, that all such revisions and modifications that are obvious to those skilled in the art will be included within the scope of the following claims:

What is claimed is as follows:

1. An elongated tube having an annular wall with an outer surface and an inner surface which inner surface defines a central passageway of a uniform size, said tube comprising a first section comprised of a first material, a second section comprised of a second material, the first and second materials being of different stiffness, and an intermediate section joining the first section and the second section, the intermediate section being a transition section in which the wall of the tube gradually changes from the first material of the first section to the second material of the second section to form a continuous unbroken tube of differential stiffness without abrupt joints, the materials of the first section and the second section naturally adhering to each other and being gradually combined in the transition section to form a wedge structure in which the first material extends into the second material within the transition section so that the second material surrounds the wedge structure of the first material and is between the wedge structure and both the inner surface and the outer surface of the wall.

2. The elongated tube of claim 1 wherein the average length of said transition section is about 0.25–20 inches.

3. The elongated tube of claim 1 wherein at least one additional material of a stiffness intermediate to the stiffness of said first and said second materials is gradually combined with and between said first and said second materials in the transition section to form a wedge structure in which said additional material extends into said first material and said second material extends into said additional material.

4. The elongated tube of claim 1 in which the wedge structure comprises a plurality of longitudinally extending spear points of the first material extending into the second material in the wall of the transition section, wherein the spear points have downstream ends circumferentially spaced apart in the wall of the transition section and gradually increase in size in the upstream direction until they join to form an annular wedge structure.

5. The elongated tube of claim 1 in which the wedge structure is formed by a plurality of elements of the first material which elements are circumferentially spaced apart in the wall of the transition section of the tube.

6. The elongated tube of claim 5 in which the ends of the elements of the first material that forms the wedge structure are spaced from both the inner surface and the outer surface of the wall of the tube.

7. A tubular strain relief insert for preventing kinking at or near a joint between a flexible tubing and a rigid fitting, said strain relief insert comprising the elongated tube of claim 1.

8. A non-kinking joint assembly for tubing, said joint assembly comprising a rigid fitting; a flexible tubing coaxial with said fitting and extending distally therefrom; and a tubular strain relief insert comprising the elongated tube of claim 1 jacketing said flexible tubing, wherein a portion of the first section of said elongated tube is disposed between said flexible tubing and said fitting and the transition and second sections of said elongated tube extend distally about said flexible tubing from said first section, providing graduated flexibility to said joint.

9. An elongated tube suitable for insertion into a quick-connect fitting comprising the elongated tube of claim 1 having a plurality of first sections, each pair of first sections having a second section therebetween joined to each of said first sections by a transition section to form a continuous unbroken tube of differential stiffness without abrupt joints.

10. A medical catheter having a shaft comprising the elongated tube of claim 1.

11. A multi-lumen catheter comprising the catheter of claim 10 wherein said tube wall defines at least one additional passageway.

12. The catheter of claim 10 further comprising a circumferential layer of braided metal mesh embedded in said wall in at least a portion of said catheter.

13. The catheter of claim 10 further comprising a helically wound metal coil embedded in said wall in at least a portion of said catheter.

14. A soft-tip guiding catheter comprising the catheter of claim 10 wherein said transition section is curved in its relaxed state and said first section is sufficiently soft to provide a low-trauma distal tip for said guiding catheter.

15. An angiographic catheter comprising the catheter of claim 10 wherein the axis of said first section is curved in its relaxed state.

16. The angiographic catheter of claim 15 wherein said tube wall is perforated in said transition section to provide medication dispensing apertures.

17. A coated guidewire for use with a medical catheter, said coated guidewire comprising a guidewire having a proximal end of uniform stiffness throughout its length and a distal end tapered to decrease its stiffness in the distal direction; said coated guidewire further comprising a jacket about said guidewire comprising the elongated tube of claim 1, said jacket providing further differential stiffness along the length of said coated guidewire.

18. A coated guidewire of claim 17 wherein said jacket further provides a substantially uniform outer diameter along the length of said coated guidewire.

19. A coated cable comprising a cable of uniform stiffness throughout its length and a jacket about said cable comprising the elongated tube of claim 1, said jacket providing differential stiffness along the length of said coated cable.

20. A unit of bump tubing having a bell end and an insert end, said bump tubing unit comprising the elongated tube of claim 1, wherein said insert end is provided by said stiffer second section of said tube and said bell end is provided by said first section, said first material of said first section being sufficiently soft to grip an insert end of another unit of said bump tubing.

21. The elongated tube of claim 1 in which the second material surrounds the wedge structure of the first material and forms both the inner surface and the outer surface of the tube wall within the transition section.

22. The elongated tube of claim 21 in which the wedge structure is formed by a plurality of elements of the first material which elements are circumferentially spaced apart in the wall of the tube.

23. The elongated tube of claim 22 in which the ends of the elements of the first material forming the wedge structure are spaced from both the inner surface and the outer surface of the wall of the tube.

24. The elongated tube of claim 1 in which the first section is comprised primarily of the first material with the first material forming the inner surface of the wall of the first section but the second material forms the outer wall of the first section, and the second section is comprised primarily of the second material with the second material forming the outer surface of the wall of the second section but the first material forms the inner wall of the second section.

25. An elongated tube having an annular wall with an outer surface and an inner surface which inner surface defines a central passageway of a uniform size, said tube comprising a first section comprised primarily of a first material that forms the inner surface of the wall, a second section comprised primarily of a second material that forms the outer surface of the wall, the first and second materials being of different stiffness, and an intermediate section joining the first section and the second section, the intermediate section being a transition section in which the wall of the tube gradually changes from the primary material of the first section to the primary material of the second section to form a continuous unbroken tube of differential stiffness without abrupt joints, the materials of the first section and the second section naturally adhering to each other and being gradually combined in the transition section to form a structure in which the first material continues to form the inner surface of the wall of the tube within the transition section and the second material continues to form the outer surface of the wall of the tube within the transition section.

26. The elongated tube of claim 25 in which the first material continues into the second section and continues to form the inner surface of the wall in the second section and the second material continues into the first section and continues to form the outer surface of the wall in the first section.

* * * * *